United States Patent [19]
Metcalf et al.

[11] 3,966,824
[45] June 29, 1976

[54] p,p'-DISUBSTITUTED α-TRICHLOROMETHYLBENZYLPHENYL ETHERS

[75] Inventors: Robert L. Metcalf; Inder Kapoor; Asha Hirwe, all of Urbana, Ill.

[73] Assignee: University of Illinois Foundation, Urbana, Ill.

[22] Filed: Nov. 29, 1974

[21] Appl. No.: 528,351

Related U.S. Application Data

[62] Division of Ser. No. 318,206, Dec. 26, 1972, Pat. No. 3,894,092.

[52] U.S. Cl. .......................... 260/612 R; 260/613 R
[51] Int. Cl.² .......................................... C07C 43/20

[58] Field of Search .................... 260/612 R, 613 R

[56] References Cited
UNITED STATES PATENTS
3,787,505    1/1974    Metcalf et al. .................. 260/612 R Primary Examiner—Bernard Helfin
Attorney, Agent, or Firm—Merriam, Marshall, Shapiro & Klose

[57] ABSTRACT p,p'-disubstituted α-trichloromethylbenzylphenyl ethers are a new class of compounds which show varying degrees of utility as selective or nonselective biodegradable insecticides and/or larvicides.

5 Claims, No Drawings

P,P'-DISUBSTITUTED α-TRICHLOROMETHYLBENZYLPHENYL ETHERS

This is a division of application Ser. No. 318,206, filed Dec. 26, 1972 and now U.S. Pat. No. 3,894,092.

SUMMARY OF THE INVENTION

The present invention relates to new compositions of matter. In particular, it concerns p,p'-disubstituted α-trichloromethylbenzylphenyl ethers some of which exhibit selective or nonselective insecticidal and/or larvicidal properties, as well as greater or lesser degrees of biodegradability.

BACKGROUND OF THE INVENTION

The p,p'-disubstituted α-trichloromethylbenzylphenyl ethers of the present invention are a novel class of compounds. Their properties are such that they exhibit utilities as selective or nonselective insecticides and/or larvicides. In addition, many of the members of the class of compounds of the present invention also exhibit properties of biodegradability. In view of the fact that DDT [1, 1, 1 trichloro-2,2-bis(p-chlorophenyl)ethane], the insecticide in most widespread use today, is not biodegradable, these properties take on added importance by serving to minimize one of the greatest deficiencies of prior art insecticides.

There is growing concern about the continuing liberation of vast quantities of DDT into the environment. The very qualities which make DDT such an effective contact or residual insecticide, i.e., its very low water solubility and high lipid solubility, caused by the nonpolarity of the DDT molecule, result in its accumulation in the fatty or lipid tissues of animals. These properties result in ever increasing concentrations in the tissues of carnivorous animals at the upper ends of food chains. The problems associated with this magnification phenomenon are further intensified by the enzymatic metabolic conversion of DDT to the even more stable dehydrochlorination product, DDE [1,1-dichloro-2,2-bis(p-chlorophenyl) ethylene].

Drug metabolizing enzymes, known as multifunction oxidases (MFO), which play a dominant role in detoxifying insecticides in both insects and higher animals, such as birds, fish, and mammals do not function on DDT and its metabolic derivatives DDE and DDD (or TDE) [1,1-dichloro-2,2-bis(p-chlorophenyl)ethane] as substrates. This single factor accounts for their storage and accumulation in animal tissues, especially at the higher ends of food chains.

Certain known symmetrical DDT analogs, such as methoxychlor [1,1,1-trichloro-,2,2-bis(p-methoxyphenyl)ethane] and methiochlor [1,1,1-trichloro-2,2-bis-(p-methiophenyl) ethane] are readily attacked by MFO enzymes, which metabolically convert or boidegrade such analogs into environmentally acceptable products which are rapidly eliminated by animals. Thus, methoxychlor is an example of a biodegradable insecticide which is not generally accumulated in animal tissues and is, thus, a more prudent choice than DDT for a variety of uses where environmental pollution is an important factor. However, metoxychlor and other known symmetrical DDT analogs (e.g., methylchlor [1,1,1-trichloro-2,2-bis(p-methylphenyl)ethane] and methiochlor), while exhibiting satisfactory insecticidal activity towards certain species of insects, exhibit considerably less insecticidal activity than DDT towards other species of insects.

One attempt to remedy the problems of the prior art is disclosed in the copending application of Metcalf et al., "Insecticidal Biodegradable Analogues of DDT," Ser. No. 147,241, filed May 26, 1971, and having a common assignee with the present application. These asymmetrical analogues of DDT have in general proved to be biodegradable and effective as insecticides. The compounds in accordance with the present invention, however, offer a mechanism of molecular cleavage of the -O-CH(CCl$_3$)-bonds, whereby biodegradability may be increased. In addition to biodegradability, certain of the compounds of the present invention offer outstanding toxicity as either selective or non-selective insecticides. The compounds of the present invention are further distinguished from prior art insecticides in that they breakdown upon prolonged exposure to sunlight, which would prove to be beneficial in applications where persistence of the insecticide is either not necessary or undesirable.

DESCRIPTION OF THE INVENTION

It has been found from metabolic studies on insects, and mice, using a model ecosystem and the methods described in Kapoor, et al., 18(6) J.Agr., Food Chem. 1145 (1970), Metcalf, et al., J. Environ. Sci. Technol. 709 (1971) and also in the copending application of Metcalf et al., "Insecticidal Biodegradable Analogues of DDT", Ser. No. 147,241, filed May 26, 1971, and having a common assignee with the present application, that certain p,p'-disubstituted α-trichloromethylbenzylphenyl ethers with various substituent groups are readily attacked by multifunction oxidase (MFO) enzymes, and thus are substantially biodegradable. Insecticidal activity studies involving both DDT resistant and regular strains of house flies, the blow fly, various types of mosquitoes and other insects have further indicated that the compounds of the present invention are effective insecticides.

The compounds of the present invention are p,p'-disubstituted α-trichloromethylbenzylphenyl ethers. Preferably, the two p,p' substituent groups are chosen from the group consisting of Cl, CH$_3$, CH$_3$O, and C$_2$H$_5$O. These compounds are biodegraded and metabolically converted to environmentally acceptable products by attack by MFO enzymes on the various substituents of the aryl rings to produce water-partitioning moieties. Also, further biodegradability is provided by separation of the two aryl rings by cleavage of the -O-CH(CCl$_3$)-bond, which is not present in DDT or its symmetrical or asymmetrical analogues. The presence of an oxygen atom between the two aryl rings of the compounds of the invention provides a means of increasing biodegradability ad does not destroy toxicity to insects.

Such p,p'-disubstituted α-trichloromethylbenzylphenyl ethers may be synthesized by condensing the appropriate α-trichloromethylbenzyl alcohol (DDT-type carbinol) with equimolar quantities of the appropriate phenol using concentrated sulfuric acid or polyphosphoric acid as the condensing agent.

EXAMPLE I

α-trichloromethyl-p-chlorobenzyl alcohol, 5.0g, was stirred with p-chlorophenol, 2.6g, and sulfuric acid, 35 ml, was added dropwise. After 2 hrs. of stirring, the mixture was poured onto ice and extracted with ether.

After drying with sodium sulfate, the ether was removed under vacuum and the residue was recrystallized from ethanol to give α-trichloromethyl-p-chlorobenzyl p-chlorophenyl ether, mp 101°C. This method of synthesis is referred to in Table I as method A.

EXAMPLE II

α-trichloromethyl-p-methoxybenzyl alcohol, 5.0g, and p-methoxyphenol, 2.48g, were added to a mixture of phosphorus pentoxide, 18g, and phosphoric acid, 12 ml, and heated for 1 hr. on the steam bath. After standing overnight, ice was added and the mixture extracted with ether. The product was purified by column chromatography on silica gel and eluted with 5% ether in petroleum ether (60°–68°C) to give α-trichloromethyl-p-methoxybenzyl p-methoxyphenyl ether, mp 90°C. This method of synthesis is referred to in Table I as method B.

Employing similar techniques, other compounds of the present invention were prepared. The properties and structures are set forth in Table I.

The compounds of the present invention were tested for insecticidal activity by standard methods, and compared with the insecticidal activities of DDT and symmetrical analogs of DDT, such as methoxychlor. Toxicological methods for the determination of the topical $LD_{50}$ values to adult female $S_{NAIDM}$ and $P_{SR}$ houseflies, Musca domestica L. and to Phormia regina, and $LC_{50}$ values to clex pipiens quinquefasciatus Say, and Anopheles albimanus Weid mosquitoes were described by Metcalf et al., 44 Bull. World Health Org. 363 (1971). The methods for evaluation of metabolism by mouse liver homogenate and by female $R_{SP}$ housefly and salt-marsh caterpillar larvae Estigmene acrea Drury, were described by Metcalf et al., 5 J. Environ. Sci. Tech. 709 (1971). The results are detailed in Table II.

TABLE I

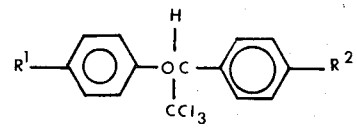

Chemical Structures and Properties of α-Trichloromethylbenzylphenyl Ethers

| $R^1$ | $R^2$ | mp °C | Method of synthesis | nmr data, α δ ppm |
|---|---|---|---|---|
| Cl | Cl | 101 | A | α-H 5.4 (s) |
| $CH_3O$ | $CH_3O$ | 90 | B | α-H 5.36 (s), $OCH_3$ 3.36 (s), 3.8 (s) |
| $CH_3$ | $CH_3$ | Liquid | B | α-H 5.41 (s), $CH_3$ 2.33 (s), $CH_3$ 2.83 (s) |
| $C_2H_5O$ | $C_2H_5O$ | Liquid | B | α-H 5.21 (s), $OCH_2$ 3.61–4.13 (m), $CH_3$ 1.2–1.5 (m) |
| Cl | $CH_3O$ | 90 | B | α-H 5.43 (s), $OCH_3$ 3.43 (s) |
| Cl | $C_2H_5O$ | Liquid | A | α-H 5.43 (s), $OCH_2$ 3.83–4.2 (q), $CH_3$ 1.26–1.5 (t) |
| $CH_3O$ | $C_2H_5O$ | 80 | B | α-H 5.43 (s), $OCH_2$ 3.85–4.2 (q), $CH_3$ 1.3–1.5 (t), $OCH_3$ 3.73 (s) |
| $CH_3$ | $C_2H_5O$ | Liquid | B | α-H 5.32 (s), $CH_3$ 2.16 (s), $OCH_2$ 3.75–4.1 (q) $CH_3$ 1.2–1.46 (t) |
| $CH_3$ | $CH_3O$ | 142 | B | α-H 5.62, $CH_3$ 2.33 (s), $OCH_3$ 3.83 (s) |

TABLE II

Toxicity of α-Trichloromethylbenzylphenyl Ethers to Insects
Topical $LD_{50}$ μg per g for

| | Substituents | | Musca domestica | | | | | | Phormia regina | | | $LC_{50}$ ppm | |
| | | | SNAIDM | | | $R_{SP}$ | | | | | | Culex fatigans larvae | Anopheles albimanus larvae |
| | $R^1$ | $R^2$ | Alone | pb | SR | Alone | pb | SR | Alone | pb | SR | | |
|---|---|---|---|---|---|---|---|---|---|---|---|---|---|
| I | Cl | Cl | 90 | 90 | 1.0 | >500 | 180 | >3.6 | >250 | >250 | — | 0.035 | 0.014 |
| II | $CH_3O$ | $CH_3O$ | 300 | 14.0 | 22 | >500 | 57.5 | >8.7 | 125 | 82.5 | 1.5 | 0.51 | 0.10 |
| III | $CH_3$ | $CH_3$ | 265 | 90 | 2.9 | >500 | 145 | >3 | 135 | 100 | 1.35 | 0.12 | 0.18 |
| IV | $C_2H_5O$ | $C_2H_5O$ | 27.0 | 13.0 | 2.1 | 42 | 24.5 | 1.7 | 16.5 | 16.5 | 1.0 | 0.11 | 0.07 |
| V | Cl | $CH_3O$ | 107.5 | 17.0 | 6.3 | 130 | 82.5 | 1.6 | 205 | 115 | 1.8 | 0.14 | 0.038 |
| VI | Cl | $C_2H_5O$ | 18.5 | 9.5 | 1.9 | 31 | 12.5 | 2.5 | 31.2 | 31.2 | 1.0 | 0.067 | 0.044 |
| VII | $CH_3O$ | $C_2H_5O$ | 45.0 | 5.0 | 9.0 | 90 | 14.0 | 6.4 | 30.0 | 16.0 | 1.9 | 0.14 | 0.034 |
| VIII | $CH_3$ | $C_2H_5O$ | 72.5 | 20.5 | 3.5 | 65 | 22.0 | 2.9 | 46.2 | 30.0 | 1.5 | 0.18 | 0.066 |
| IX | $CH_3$ | $CH_3O$ | >500 | 39.0 | >13 | >500 | 135 | >4 | >250 | >250 | — | 0.65 | >1.0 |

Compounds of the Present Invention are Effective Insecticides

The data of Table II indicate the insect toxicity of 9 different α-trichloromethylbenzylphenyl ethers to Musca domestica ($S_{NAIDM}$ and $R_{SP}$ strains), Phormia regina, and to Culex fatigans and Anopheles albimanus. The compounds with the highest intrinsic toxicity were $CH_3O$, $OC_2H_5$ (VII), Cl, $OC_2H_5$ (VI), and $C_2H_5O$, $OC_2H_5$ (IV). The $CH_3O$, $OCH_3$ compound (II) had the largest SR value in both susceptible and resistant houseflies (22->8.7), indicating rapid detoxication, while the Cl, $OC_2H_5$ compound (VI) had the lowest SR values (1.9-2.5).

The most effective insecticide generally was VI ($\alpha$-trichloromethyl-p-ethoxybenzyl p-chlorophenyl ether) which had the lowest $LD_{50}$ values to the housefly and was only slightly less toxic to Phormia than the p,p'-diethoxy compound IV and to mosquito larvae than compound I. Toxicity in the symmetrical substituents was in the general order of $C_2H_5O > Cl > CH_3O > CH_3$.

The synergistic ratios or SR values ($LD_{50}$ alone/ $LD_{50}$ synergized with piperonyl butoxide) shown in Table II indicate the role of the multifunction oxidase (MFO) in detoxifying the individual compounds. Since piperonyl butoxide serves to block the action of MFO, the synergized $LD_{50}$ values express the intrinsic toxicity of the compounds. With the detoxifying action of MFO enzymes blocked, the intrinsic toxicity of the compounds can thus be measured. For the *Musca domestica* $S_{NAIDM}$, the compounds with the highest intrinsic toxicity were $CH_3O$, $C_2H_5$(VII), Cl, $C_2H_5O$ (VI) $C_2H_5O$, $OC_2H_5$ (IV) and $CH_3O$, $CH_3O$ (II), having synergized $LD_{50}$ values of 5.0, 9.5, 13.0, and 14.0 respectively. Compounds IV and VII were quite toxic to Phormia, which is dificient in MFO, with synergized $LD_{50}$ values of 16.5 and 16.0 respectively. As a larvicide Cl, Cl (I) was the most toxic, with an $LC_{50}$ ppm of 0.035 and 0.014 for *Culex fatigans* and *Anopheles albimanus* respectively.

Employing the techniques disclosed in Metcalf et al., 5 J. Environ. Sci. Technol. 709 (1971), the compounds of the present invention have been shown to be biodegradable.

The foregoing detailed description has been given for clearness of understanding only, and no unnecessary limitations should be understood therefrom as modifications will be obvious to those skilled in the art.

What is claimed is:

1. Insecticides having the formula

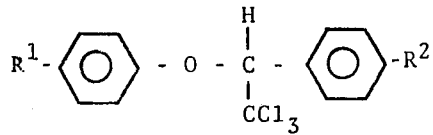

where $R^1$ and $R^2$ are selected from the group consisting of substituents Cl, $CH_3$, $CH_3O$, and $C_2H_5O$, provided that at least one of $R^1$ and $R^2$ in Cl or $CH_3$.

2. An insecticide as claimed in claim 1 wherein $R_1$ is Cl.

3. An insecticide as claimed in claim 1 wherein $R_1$ is $CH_3$.

4. An insecticide as claimed in claim 1 wherein $R_2$ is Cl.

5. An insecticide as defined by claim 1 wherein $R_2$ is $CH_3$.

* * * * *